United States Patent [19]

Braquet et al.

[11] Patent Number: 4,923,870
[45] Date of Patent: May 8, 1990

[54] 2-CARBONYL SUBSTITUTED N,N'-DI-(TRIMETHOXYGENZOYL)PIPERAZINES, PROCESS FOR PREPARING THE SAME AND THERAPEUTICAL COMPOUNDS CONTAINING THEM

[75] Inventors: Pierre Braquet, Garches, France; Georges Dive, Tilff, Belgium; Jean-Jacques Godfroid; Francoise Heymans; Eduardo Pirotzky, all of Paris, France

[73] Assignee: Societe de Conseils de Reserches et d'Applications Scientifiques, France

[21] Appl. No.: 418,114

[22] Filed: Oct. 6, 1989

[30] Foreign Application Priority Data

Oct. 11, 1988 [GB] United Kingdom ............... 8823775

[51] Int. Cl.$^5$ .................. A61K 31/495; C07D 241/04
[52] U.S. Cl. .................................. 514/255; 514/183; 514/212; 540/481; 540/598; 544/360; 544/387
[58] Field of Search ............... 544/387, 359, 360; 514/255, 183, 212; 540/481, 598

[56] References Cited

U.S. PATENT DOCUMENTS 3,186,993 6/1965 Knapp ........................... 544/387
3,933,802 2/1976 Ferrini et al. ................. 544/387

Primary Examiner—Richard L. Raymond
Assistant Examiner—James H. Turnipseed
Attorney, Agent, or Firm—Lucas & Just

[57] ABSTRACT

This invention relates to piperazine derivatives having the general formula I:

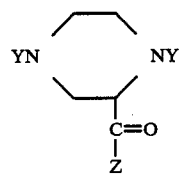

wherein Y stands for

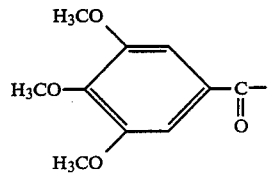

and Z represents various substituents, to be a preparation process of said compounds and to therapeutic compositions containing them as an active ingredient.

3 Claims, No Drawings

2-CARBONYL SUBSTITUTED N,N'-DI-(TRIMETHOXYGENZOYL)PIPERAZINES, PROCESS FOR PREPARING THE SAME AND THERAPEUTICAL COMPOUNDS CONTAINING THEM

This invention relates to piperazine derivatives having the general formula I:

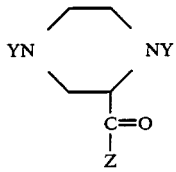

I wherein Y stands for

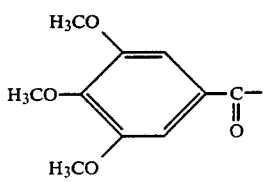

and Z represents
either a substituent OA wherein A represents a straight or branched alkyl chain having from 1 to 12 carbon atoms; a cycloalkyl group having from 5 to 10 carbon atoms or a group of the general formula:

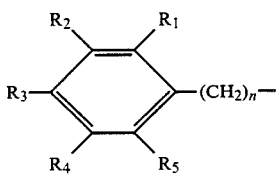

wherein n is zero or an integer of from 1 to 5 and either each of $R_1$, $R_2$, $R_3$, $R_4$ and $R_5$ independently represents a hydrogen, chlorine or bromine atom, trifluoromethyl, trifluoromethoxy or trifluoromethylthio, methyl or methoxy group,
or a substituent

wherein $A_1$ and $A_2$ independently represent a hydrogen atom or, the same groups A as above defined or $A_1$ and $A_2$ together form a cycloalkyl group having from 5 to 10 carbon atoms.

The invention also relates to a preparation process of compounds of formula I, said process comprising reacting a compound of formula II:

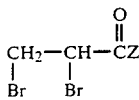

II wherein Z is as above defined, with equimolar quantity of N,N'-dibenzylethylenediamine. The reaction is suitably carried out in an aprotic solvent (such as benzene or toluene) at 80° C. in the presence of triethylamine. The trisubstituted piperazine obtained of formula III:

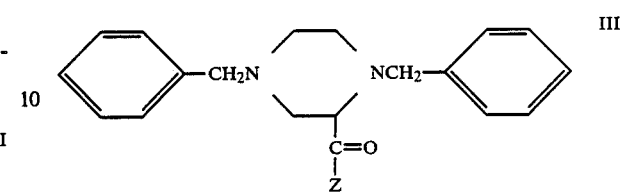

III is then hydrogenolized in the presence of Pd/charcoal in a solvent such as ethanol at 40° C. under pressure and the corresponding monosubstituted piperazine obtained of formula IV:

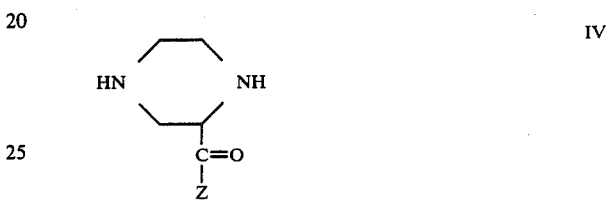

IV is then di substituted by treatment with 3,4,5-trimethoxybenzoyl chloride in a solvent such as benzene and in the presence of triethylamine, at room temperature.

The starting material of the general formula II may be prepared by treating the corresponding ethylenic compound of general formula V:

V with bromine.

The invention finally relates to therapeutic compositions containing one of the compounds I as an active ingredient therein. These compounds are active in the anti-ischemic and anti-inflammatory field.

EXAMPLE 1

N,N'-di-(3',4',5'-trimethoxybenzoyl)-2-n-hexyloxycarbonyl piperazine $Z=O-(CH_2)_5-CH_3$ Step A
Preparation of N,N'-dibenzyl 2-n-hexyloxycarbonyl piperazine (III, $Z=O(CH_2)_5CH_3$).

A solution of 48.5 g (154 mmoles) of n-hexyl 2,3-dibromopropionate (II, $Z=O(CH_2)_5CH_3$) in 100 ml of dry benzene stirred at 40° C. is added dropwise to a warm solution (80° C.) of 37 g (154 mmoles) of N,N'-dibenzylethylenediamine and 55 ml of triethylamine in 100 ml benzene. The mixture was stirred for 3 hours at 80° C. After cooling and filtration of the triethylammonium chloride, the solution was evaporated off and the crude residue treated with diethyl ether and washed with water. The organic layer was dried (MgSO$_4$), evaporated and chromatographed on a silica gel column using diethyl ether/petroleum ether (10:90, in vol.) as eluent, yielding 52.5 g (86.5%) of the title compound as an oil.

IR (film): 3080, 3060, 3030 (Aromatic C—H), 2940, 2800 (C—H), 1740 (C=O), 1600 (Aromatic C=C), 1145 (C—O) cm$^{-1}$.

$^1$HNMR (80 MHz, CDCl$_3$, HMDS) δ ppm: 7.25 (large s, 10H, ArH), 4.17 (t, 2H, CH$_2$OC=O), 4.01–3.41 (m, 4H, CH$_2$Φ), 3.37–2.12 (m, 7H, piperazinyl), 1.5 (m, 2H, CH$_2$—C—OC=O), 1.2 (large s, 6H, (CH$_2$)$_3$), 0.80 (t, 3H, CH$_3$).

Step B

Preparation of 2-n-hexyloxycarbonyl piperazine (IV, Z=O(CH$_2$)$_5$CH$_3$)

A solution of 25 g (63.5 mmoles) of the compound prepared in step A and 200 mg Pd(10%)/charcoal in 200 ml of ethanol was treated by H$_2$ under pressure of 2.8 bars under stirring at 40° C. overnight. After filtration, the ethanol was evaporated off under reduced pressure and the crude residue, purified on a silica gel column using MeOH/CHCl$_3$ (5:95, in vol.) as eluent, yielded 12.5 g (92%) of the title compound as a highly hygroscopic compound.

IR (film): 3195 (N—H), 2930, 2850 (C—H), 1735 (C=O) cm$^{-1}$.

$^1$HNMR (80 MHz, CDCl$_3$, HMDS) δ ppm: 4.2 (t, 2H, CH$_2$OC=O), 3.53–3.23 (m, 1H, CH—C=O), 3.17–2.65 (m, 6H, CH$_2$ piperazine), 1.90 (s, 2H, NH), 1.5 (m, 2H, CH$_2$—C—OC=O), 1.22 (large s, 6H, (CH$_2$)$_3$), 0.85 (t, 3H, CH$_3$).

Step C

Preparation of N,N'-di-(3',4',5'-trimethoxybenzoyl)-2-n-hexyloxycarbonyl piperazine (I, Z=O(CH$_2$)$_5$CH$_3$)

A solution of 10 g (47 mmoles) of the compound prepared in step B in 150 ml of dry benzene and 25 ml of triethylamine was added dropwise to a solution of 22.7 g (99 mmoles) of 3,4,5-trimethoxybenzoyl chloride in 50 ml of dry benzene. The mixture was kept stirring at room temperature overnight. The excess of acylchloride was then decomposed by the addition of 5 ml EtOH. After evaporation of the solvents under reduced pressure, the residue was treated by CHCl$_3$, washed with H$_2$O, diluted NaHCO$_3$ then H$_2$O. After drying (MgSO$_4$) and evaporation of the chloroform, a purification on a silica gel column using MeOH/CHCl$_3$ (0.5:99.5, in vol.) yielded 25 g (88%) of a syrup which crystallized in diethyl ether; mp=142.2° C.

IR (film): 3010 (ArC—H), 2940, 2860 (C—H), 1740 (C=O ester), 1645 (C=O amide), 1590 (ArC=C) cm$^{-1}$.

$^1$HNMR (80 MHz, CDCl$_3$, HMDS) δ ppm: 6.65 (s, 4H, ArH), 4.85 (m, 1H, CHC=O), 4.12 (m, 4H, CH$_2$OC=O and O=C—NCH$_2$—C—C=O), 3.82 (s, 18H, CH$_3$O), 3.62–3.05 (m, 4H, O=C—N—CH$_2$), 1.58 (m, 2H, CH$_2$—C—C=O), 1.21 (large s, 6H, (CH$_2$)$_3$), 0.81 (t, 3H, CH$_3$).

EXAMPLE 2

N,N'-di-(3',4',5'-trimethoxybenzoyl)-2-ethoxycarbonyl piperazine

Z=OCH$_2$CH$_3$

The title compound was obtained as described in example 1, steps A, B, C but starting with ethyl 2,3-dibromopropionate instead of n-hexyl 2,3 dibromopropionate; white crystals, m.p=129.5° C.

IR (film): 3010 (ArC—H), 2940, 2830 (C—H), 1735 (C=O ester), 1635 (C=O amide), 1580 (ArC=C) cm$^{-1}$.

$^1$HNMR (60 MHz, CDCl$_3$, HMDS) δ ppm: 6.66 (s, 4H, Aromatic H), 4.86 (m, 1H, CHC=O), 4.13 (m, 4H, CH$_2$OC=O+O=CN—CH$_2$—C—C=O), 3.9 (s, 18H, CH$_3$O), 3.6–2.88 (m, 4H, CH$_2$—NCO), 0.9 (t, 3H, CH$_3$).

EXAMPLE 3

N,N'-di-(3',4',5'-trimethoxybenzoyl)-2-(2'-isopropyl 5'-methyl)-cyclohexyloxycarbonyl piperazine

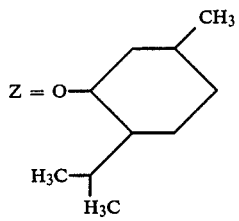

The title compound was obtained as described in example 1, steps A, B, C but starting with (2'-isopropyl 5'-methyl)-cyclohexyl 2,3-dibromopropionate; white crystals, mp=151.9° C.

IR (nujol): 1740 (C=O ester), 1645 (C=O amide), 1585 (ArC=O) cm$^{-1}$.

$^1$HNMR (80 MHz, CDCl$_3$, HMDS) δ ppm: 6.67 (m, 4H, ArH), 5.3 (m, 1H, CHOC=O), 4.87 (m, 1H, CHC=O), 4.15 (m, 2H, O=CN—CH$_2$—C—C=O), 3.67–2.75 (m, 4H, CH$_2$NC=O), 2.17–1.11 (m, 9H, CH$_2$ of the cyclohexyl+(CH$_3$)$_2$CH), 0.87 (m, 9H, CH$_3$).

EXAMPLE 4

N,N'-di-(3',4',5'-trimethoxybenzoyl)-2-(N-orthochlorophenyl)amido piperazine

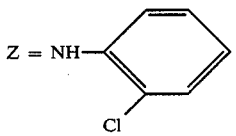

The title compound was obtained as described in example 1 steps A, B, C but starting from 2'-chlorophenyl 2,3-dibromopropionamide instead of n-hexyl 2,3-dibromopropionate; white crystals, mp: 144.2° C.

IR (film): 3280 (N—H), 3070 (ArC—H), 2950, 2840 (C—H), 1710 (O=CNAr), 1635

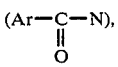

1590 (ArC=C) cm$^{-1}$.

$^1$HNMR (80 MHz, CDCl$_3$, HMDS) δ ppm: 8.27 (m, 1H, NH), 7.5–6.9 (m, 4H, orthochlorophenyl), 6.77 (d, 4H, trimethoxybenzoyl ArH), 5.22 (m, 1H, CHCON), 4.47–4.05 (m, 2H, O=CN—CH$_2$—C—C=O), 3.87 (s, 18H, CH$_3$O), 3.65–2.95 (m, 4H, CH$_2$NCO).

EXAMPLE 5

N,N'-di-(3',4',5'-trimethoxybenzoyl)-2-(N-n-hexyl)-amido piperazine

Z=NH—(CH$_2$)$_5$CH$_3$

The title compound was obtained as described in example 1 steps A, B, C but starting from n-hexyl 2,3-dibromopropionamide; white crystals, mp=189.2° C.

IR (film): 3330 (N—H), 3010 (ArC—H), 2940, 2820 (C—H), 1665 (AlNC=O), 1635 (ArNC=O), 1590 (ArC=C) cm$^{-1}$.

$^1$HNMR (80 MHz, CDCl$_3$, HMDS) δ ppm: 6.71 (large s, 5H, ArH+NH), 4.8 (m, 1H, CHCON), 4.72–3.97 (m, 2H, O=CN—CH$_2$—C—C=O), 3.47–2.97 (m, 6H, CH$_2$CON+CH$_2$NCO), 1.70–1.08 (m, 8H, (CH$_2$)$_4$), 0.82 (t, 3H, CH$_3$).

EXAMPLE 6

According to the same process as described in Example 1, steps A, B, C, the following compound was prepared (only modification of the $^1$HNMR spectrum is given):

N,N'-di-(3',4',5'-trimethoxybenzol)-2-N''-benzylamido piperazine

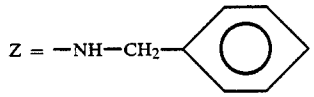

Waxycompound $^1$HNMR δ ppm: 7.22 (s, 5H, C$_6$H$_5$), 4.40 (d, 2H, NCH$_2$Φ).

TOXICOLOGY

The compounds of the invention have been administered per os to mice for determination of acute LD$_{50}$. For all the compounds of the invention, LD$_{50}$ was over 800 mg/kg.

PHARMCOLOGY

A proof of the pharmaceutical interest of the compounds of the invention has been established by the following pharmaceutical experimentation:

Inhibition of the platelets aggregation on New Zealand rabbits

The experimentation was conducted on platelets with plasma of New Zealand rabbits. Blood samples were taken from auricular artery and placed in a citrate buffer (3.8%; pH 7.4); blood was further centrifuged for 15 mn at 1200 RPM. The tested sample was prepared in DMSO, then poured on platelets rich plasma for 1 mn, then a dose of 2.5 nM of PAF was added. The determination is made on a Cronolog Coultronics apparatus which determines the transmission percentage corresponding to the maximum height of the peak before the desaggregation. The percentage of variation of the inhibition with respect to the transmission percentage is calculated (control: pure DMSO). This method was described in details in LABORATORY INVESTIGATIONS, Vol. 41, No. 3, p. 275, 1979, JEAN-PIERRE CAZENAVE, Dr. MED., JACQUES BENVENISTE, DR. MED., AND J. FRASER MUSTARD, M.D., "Aggregation of rabbits platelets by platelet-activating factor is independent of the release reaction and the arachidonate pathway and inhibited by membrane-active drugs".

The results demonstrate that the compounds inhibit the aggregation induced by 2.5 nM of PAF. Five tests made on 6 different rabbits allowe us to calculate the IC$_{50}$ of the various compounds using the linear regression test.

The values for IC$_{50}$ on platelets have been found as follows:

| | | |
|---|---|---|
| Example 1: | 2.15 | .10$^{-6}$ |
| Example 2: | 1.29 | .10$^{-6}$ |
| Example 3: | 1.6 | .10$^{-5}$ |
| Example 4: | 3.36 | .10$^{-6}$ |
| Example 5: | 8.84 | .10$^{-6}$ |
| Example 6: | 1.97 | .10$^{-5}$ |

PRESENTATION-POSOLOGY

In human therapy, active doses are 1–50 mg/kg per day in oral administration (tablets and gelatine capsules, for instance) or 0.1 to 5 mg/kg in IV. administration (unit doses of 0.1, 0.5, 1 or 1 mg in individual phiols.

We claim:

1. Piperazine derivatives having the general formula I:

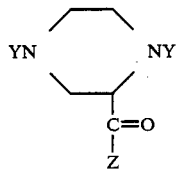

wherein Y stands for

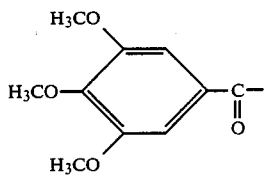

and Z represents
  either a substituent OA wherein A represents a straight or branched alkyl chain having from 1 to 12 carbon atoms; a cycloalkyl group having from 5 to 10 carbon atoms or a group of the general formula:

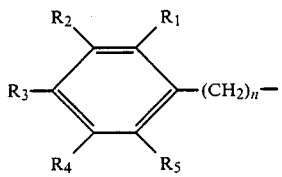

wherein n is zero or an integer of from 1 to 5 and either each of R$_1$, R$_2$, R$_3$, R$_4$ and R$_5$ independently represents a hydrogen, chlorine or bromine atom, trifluoromethyl, trifluoromethoxy or trifluoromethylthio, methyl or methoxy, group,
or a substituent

wherein $A_1$ and $A_2$ independently represent a hydrogen atom or, the same groups A as above defined or $A_1$ and $A_2$, together form a cycloalkyl group having from 5 to 10 carbon atoms.

2. Preparation process of compounds of claim 1, said process comprising reacting a compound of formula II:

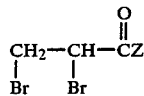

wherein Z is as above defined, with equimolar quantity of N,N'-dibenzylethylenediamine; the reaction being carried out in an aprotic solvent (such as benzene or toluene) at 80° C. in the presence of triethylamine, hydrogenolizing the trisubstituted piperazine obtained of formula III:

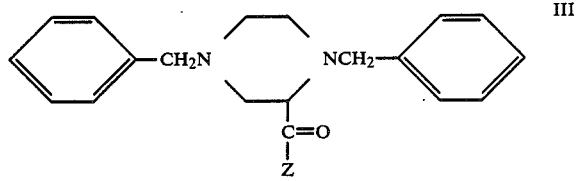

in the presence of Pd/charcoal in an alcoholic solvent at 40° C., under pressure and treating the corresponding monosubstituted piperazine obtained of formula IV:

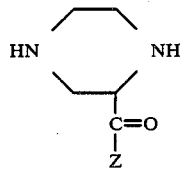

by 3,4,5-trimethoxybenzoyl chloride in benzene and in the presence of triethylamine, at room temperature.

3. A therapeutic composition of matter comprising an effective amount of, at least, one compound according to claim 1, associated with the usual excipients for the selected administration route.

* * * * *